United States Patent
Yoshida

(10) Patent No.: US 9,255,914 B2
(45) Date of Patent: Feb. 9, 2016

(54) ULTRASONIC DIAGNOSIS APPARATUS AND PROGRAM

(75) Inventor: Tetsuya Yoshida, Nasushiobara (JP)

(73) Assignees: KABUSHIKI KAISHA TOSHIBA, Tokyo (JP); Toshiba Medical Systems Corporation, Otawara-Shi (JP)

(*) Notice: Subject to any disclaimer, the term of this patent is extended or adjusted under 35 U.S.C. 154(b) by 885 days.

(21) Appl. No.: 12/855,195

(22) Filed: Aug. 12, 2010

(65) Prior Publication Data

US 2011/0040183 A1    Feb. 17, 2011

(30) Foreign Application Priority Data

Aug. 13, 2009    (JP) ................................. 2009-187819

(51) Int. Cl.
     *G01N 29/46*    (2006.01)
     *G01N 29/06*    (2006.01)
     *A61B 8/00*    (2006.01)

(52) U.S. Cl.
     CPC ............ *G01N 29/46* (2013.01); *G01N 29/0672* (2013.01); *A61B 8/00* (2013.01); *G01N 2291/02475* (2013.01)

(58) Field of Classification Search
     CPC .. A61B 8/5246; A61B 8/5238; A61B 8/5253; A61B 5/726; G01S 15/8977; G06T 2207/20064; G06T 2207/20021; G06T 2207/20221
     USPC ................................ 600/437, 440, 441, 455
     See application file for complete search history.

(56) References Cited

U.S. PATENT DOCUMENTS 5,619,998 A * 4/1997 Abdel-Malek et al. ....... 600/437
6,095,980 A * 8/2000 Burns et al. ................... 600/453

(Continued)

FOREIGN PATENT DOCUMENTS

| EP | 1146351 A1 * | 10/2001 |
| JP | 2006-116307 | 5/2006 |
| JP | 2007-513727 A | 5/2007 |
| JP | 2009-82469 | 4/2009 |

OTHER PUBLICATIONS

Sudha et al., Speckle Noise Reduction in Ultrasound Images by Wavelet Thresholding based on Weighted Variance, International Journal of Computer Theory and Engineering, vol. 1, No. 1, Apr. 2009 1793-8201.*

(Continued)

*Primary Examiner* — Katherine Fernandez
*Assistant Examiner* — Ellsworth Weatherby
(74) *Attorney, Agent, or Firm* — Oblon, McClelland, Maier & Neustadt, L.L.P.

(57) ABSTRACT

According to one embodiment, an ultrasonic diagnosis apparatus is configured as follows. Namely, the apparatus includes a first unit configured to generate a first transmission wave for acquisition of a first image with a higher priority on sensitivity than on resolution, a second unit configured to generate a second transmission wave for acquisition of a second image with a higher priority on resolution than on sensitivity, an analysis unit configured to perform multiresolution analysis based on predetermined transform processing on the first image and the second image, a filter unit configured to perform predetermined filter operation for corresponding coefficients of the first image and the second image for each coefficient of each resolution acquired by the analysis unit, and an inverse transform unit configured to generate a composite image of the first image and the second image by performing inverse transform processing of transform processing by the analysis unit.

14 Claims, 7 Drawing Sheets

(56) References Cited

U.S. PATENT DOCUMENTS

| | | | |
|---|---|---|---|
| 6,673,019 B2* | 1/2004 | Kamiyama | 600/443 |
| 6,676,606 B2* | 1/2004 | Simpson et al. | 600/458 |
| 7,236,637 B2* | 6/2007 | Sirohey et al. | 382/240 |
| 7,758,507 B2* | 7/2010 | Yoshikawa et al. | 600/441 |
| 2010/0142790 A1* | 6/2010 | Chang | 382/132 |
| 2010/0280378 A1* | 11/2010 | Nakahira et al. | 600/445 |
| 2011/0040176 A1* | 2/2011 | Razansky et al. | 600/425 |
| 2011/0079082 A1* | 4/2011 | Yoo et al. | 73/632 |

OTHER PUBLICATIONS

Biagi et al., Radiofrequency Real Time Processing: Ultrasonic Spectral Images and Vector Doppler Investigation, Acoustical Imaging, vol. 25, Edited by Halliwell and Wells. Kluwer Academic/Plenum Publishers, 2000.*

Office Action issued Jan. 21, 2014 in Japanese Patent Application No. 2010-181201 (with English language translation).

* cited by examiner

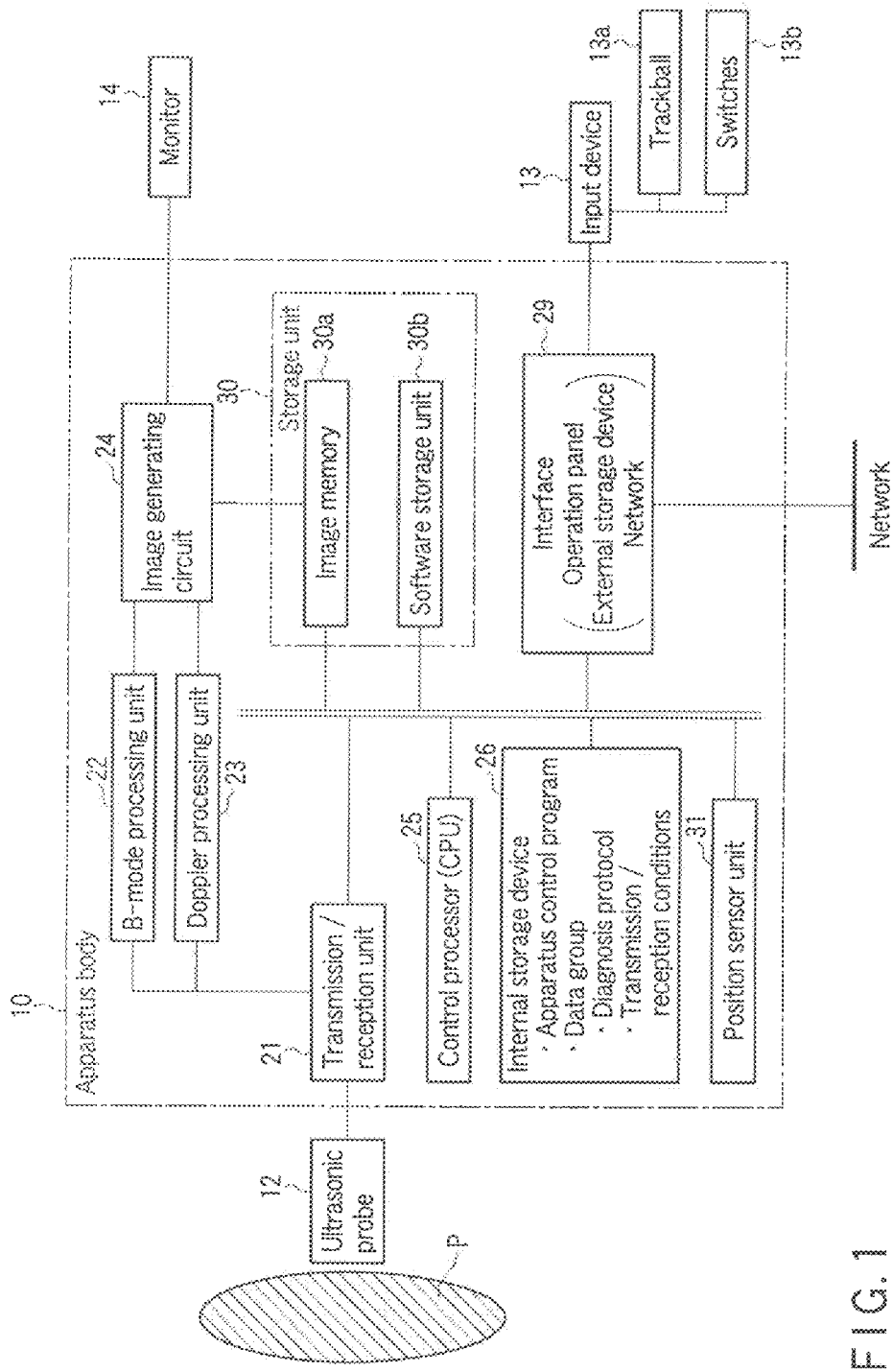
F I G. 1

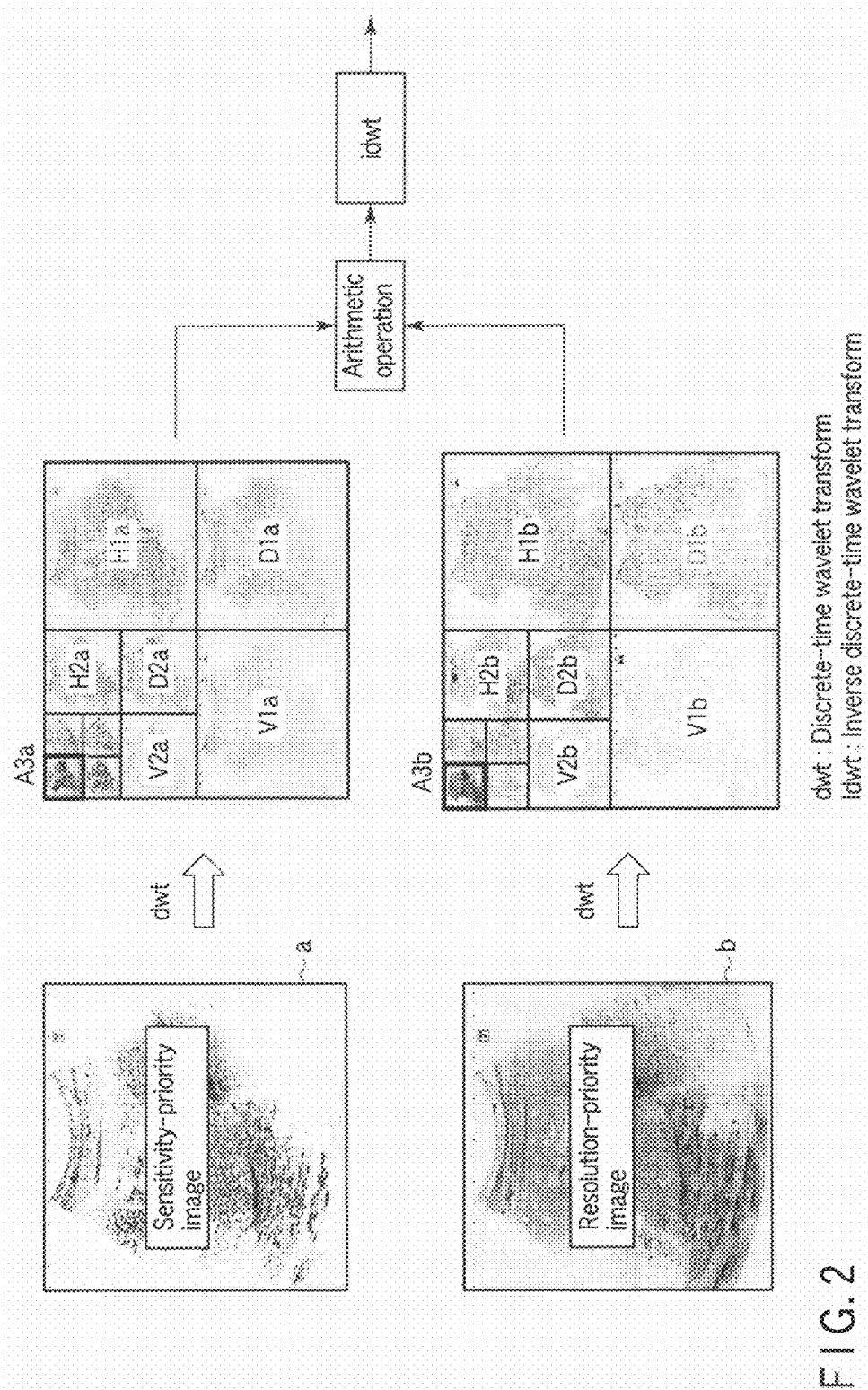
F I G. 2

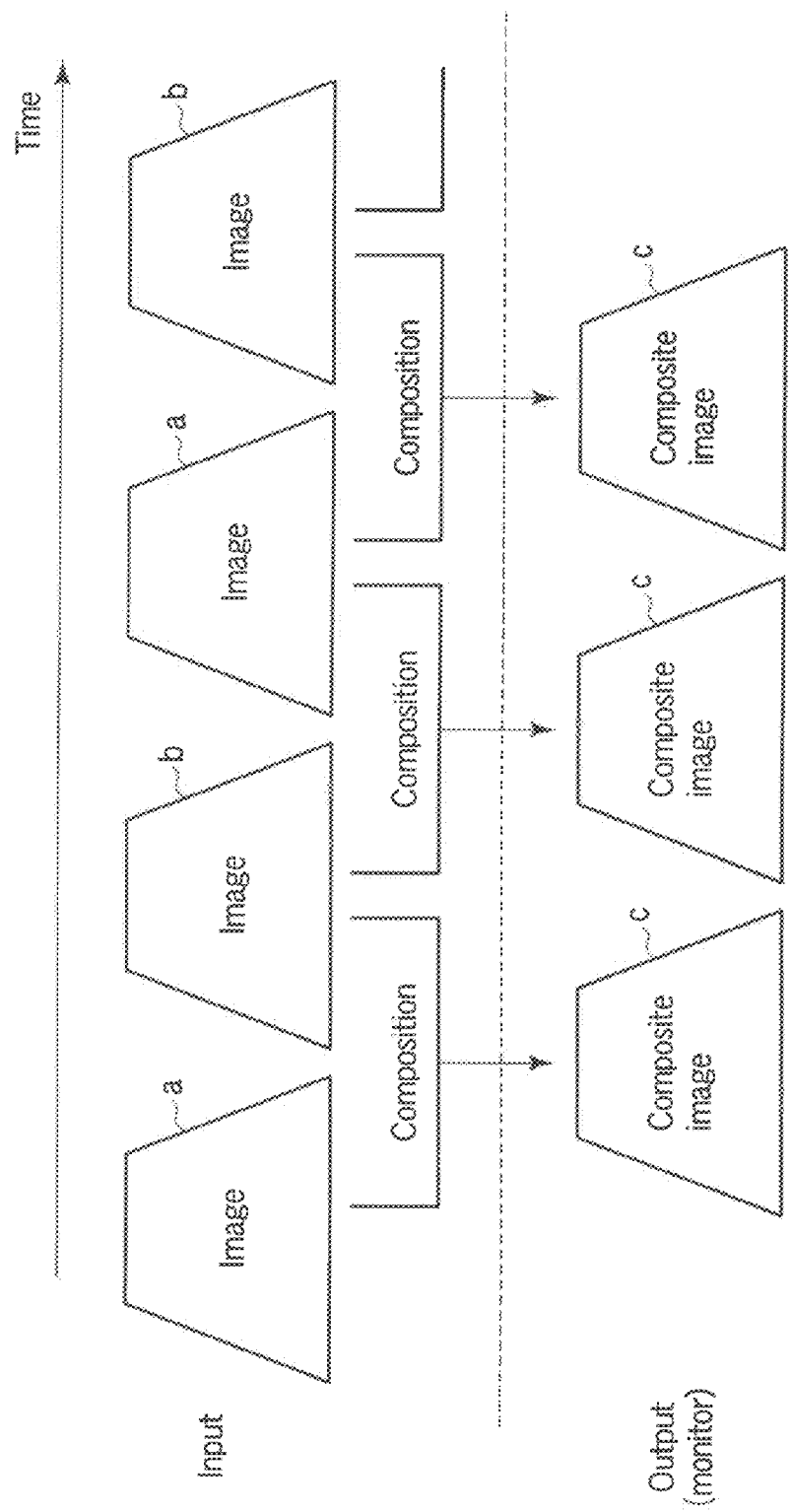
F I G. 3

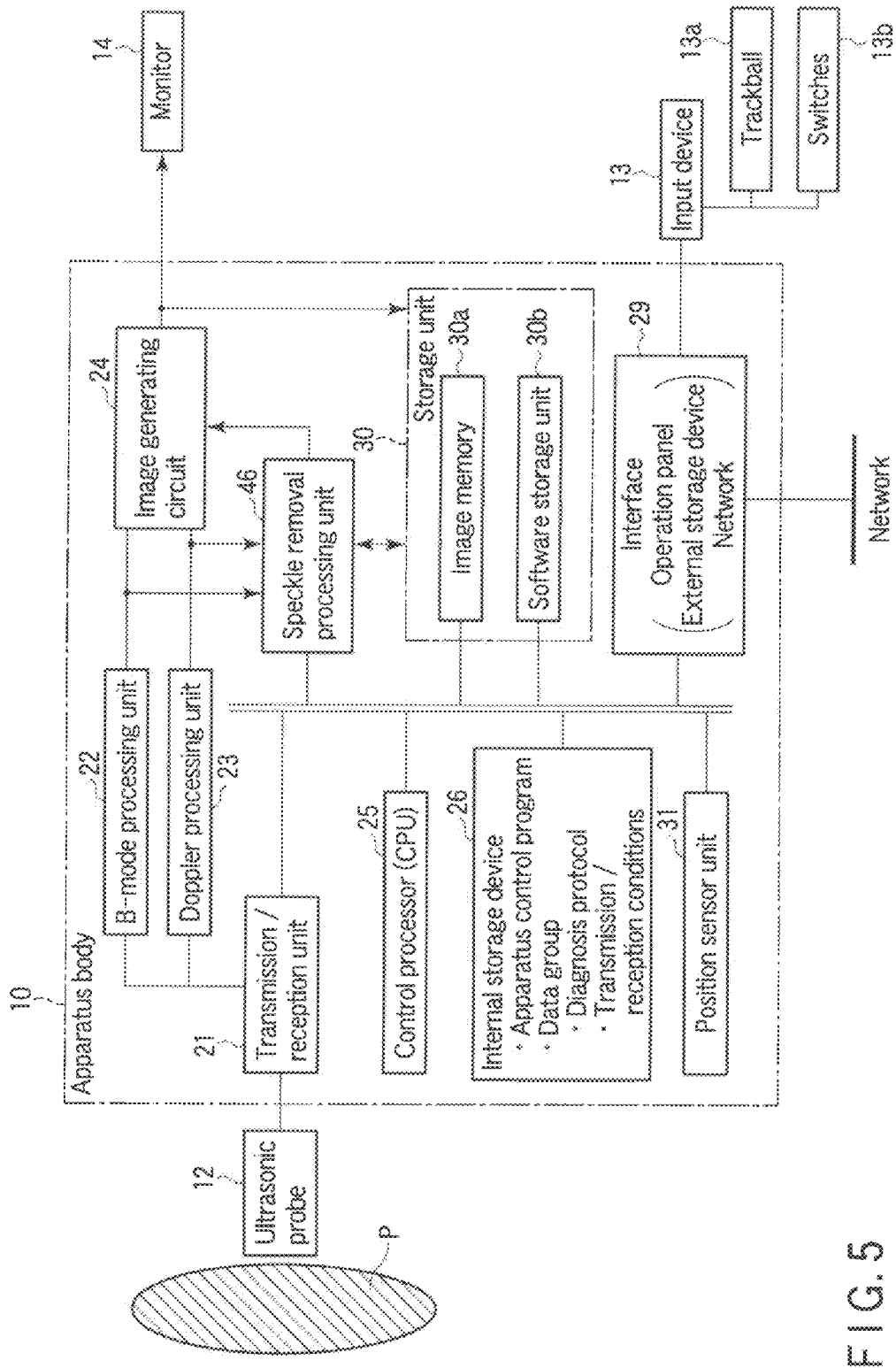
F I G. 5

ULTRASONIC DIAGNOSIS APPARATUS AND PROGRAM

CROSS-REFERENCE TO RELATED APPLICATIONS

This application is based upon and claims the benefit of priority from Japanese Patent Application No. 2009-187819, filed Aug. 13, 2009; the entire contents of which are incorporated herein by reference.

FIELD

Embodiments described herein relate generally to an ultrasonic diagnosis apparatus and a program for causing a computer to function as the ultrasonic diagnosis apparatus and, more particularly, to an ultrasonic diagnosis apparatus which acquires and displays a tissue image or a contrast-enhanced bubble image by transmitting and receiving ultrasonic waves and a program which causes a computer to function as the ultrasonic diagnosis apparatus.

BACKGROUND

Recently, ultrasonic diagnosis apparatuses have been widely used in the general medical field. An ultrasonic diagnosis apparatus allows real-time visual recognition of, for example, the pulsation of the heart of an object and the movement of a fetus with the simple operation of only bringing an ultrasonic probe into contact with the body surface of the object. The ultrasonic diagnosis apparatus is considered highly safe for human bodies, and can be repeatedly used for examination.

In addition, the ultrasonic diagnosis apparatus is smaller in system size than other medical image diagnosis apparatuses such as an X-ray diagnosis apparatus, CT apparatus, and MRI apparatus. Therefore, for example, this apparatus allows easy examination upon being moved to a bed side. More specifically, although it depends on the types of functions of the ultrasonic diagnosis apparatuses, for example, compact apparatuses which can be carried with, for example, one hand have been developed.

As described above, the ultrasonic diagnosis apparatus is free from the influence of exposure to radiation and the like and is small in size, and hence can be used for home medical care services and the like.

The ultrasonic diagnosis apparatus has a problem of so-called speckle noise caused by simultaneous occurrence of reflection and scattering of ultrasonic waves due to a medium, small bioligical tissue, or the like in an object. This speckle noise degrades not only the image quality of a video but also accuracy in the display of an important form such as the boundary between a body organ to be observed and the background. Such speckle noise is a significant trouble in fields of video interpretation, organ recognition, and the like using videos acquired by the ultrasonic diagnosis apparatus.

In order to solve this problem, for example, the following technique is disclosed in Jpn. Pat. Appln. KOKAI Publication No. 2006-116307.

That is, Jpn. Pat. Appln. KOKAI Publication No. 2006-116307 discloses a technique including a step (a) of decomposing a two-dimensional ultrasonic input video into a plurality of multiresolution videos at N (a positive integer) levels, a step (b) of determining the characteristic of each pixel of each decomposed video, a step (c) of executing image quality improvement processing for each decomposed video based on the pixel characteristics, a step (d) of executing 1-level composition of the decomposed videos, and a step (e) of repeatedly executing the steps (b) to (d) until the size of the composite video becomes equal to that of the above two-dimensional ultrasonic video. More specifically, wavelet transform is used for multiresolution analysis used in the step (a).

The technique disclosed in Jpn. Pat. Appln. KOKAI Publication No. 2006-116307 removes speckle noise and hence improves the image quality of a video acquired by the ultrasonic diagnosis apparatus.

The ultrasonic diagnosis apparatus performs imaging by transmitting ultrasonic waves from the ultrasonic probe to the inside of an object and receiving reflected signals from the inside of the object. For this reason, in the process of propagation of ultrasonic waves in an object, for example, ultrasonic waves are scattered or attenuated. That is, the deeper a region is located in an object, the more difficult to visualize it by the ultrasonic diagnosis apparatus.

More specifically, the distance resolution is superior but the depth sensitivity is inferior when the wave train length of the transmission waveform of an ultrasonic wave is short than when the wave train length is long. In addition, the higher the frequency of an ultrasonic wave, the higher the spatial resolution. However, since the degree of attenuation of the ultrasonic wave during propagation increases, the depth sensitivity decreases.

The same applies to contrast-enhanced ultrasonography. In contrast-enhanced ultrasonography, the detection sensitivity of contrast-enhanced bubbles is obviously important. The ability to visually recognize contrast-enhanced bubbles with high spatial resolution is also important in a clinical point of view because, for example, it facilitates visual recognition of the marginal information of a lesion.

As described above, in the ultrasonic diagnosis apparatus, there exists the so-called tradeoff between the sensitivity of an acquired video and the resolution, and it is very difficult to satisfy both the requirements.

Note that the technique disclosed in Jpn. Pat. Appln. KOKAI Publication No. 2006-116307 is not a technique that solves this problem.

The present invention has been made in consideration of the above situation, and has as its object to provide an ultrasonic diagnosis apparatus and program which can acquire a video that satisfies both the requirements for sensitivity (luminance) and resolution (visibility).

BRIEF DESCRIPTION OF THE DRAWINGS

FIG. 1 is a block diagram showing the system configuration of an ultrasonic diagnosis apparatus according to an embodiment of the present invention;

FIG. 2 is a view showing the principle of image composition processing by an image generating circuit 24 in an ultrasonic diagnosis apparatus 10 according to this embodiment;

FIG. 3 is a view for explaining the processing of acquiring images a and b by switching transmission waves alternately for each frame, and generating a composite image c by performing the above image composition processing between two consecutive frames;

FIG. 5 is a block diagram showing an example of the system configuration of an ultrasonic diagnosis apparatus according to a modification;

DETAILED DESCRIPTION

Figure 4:
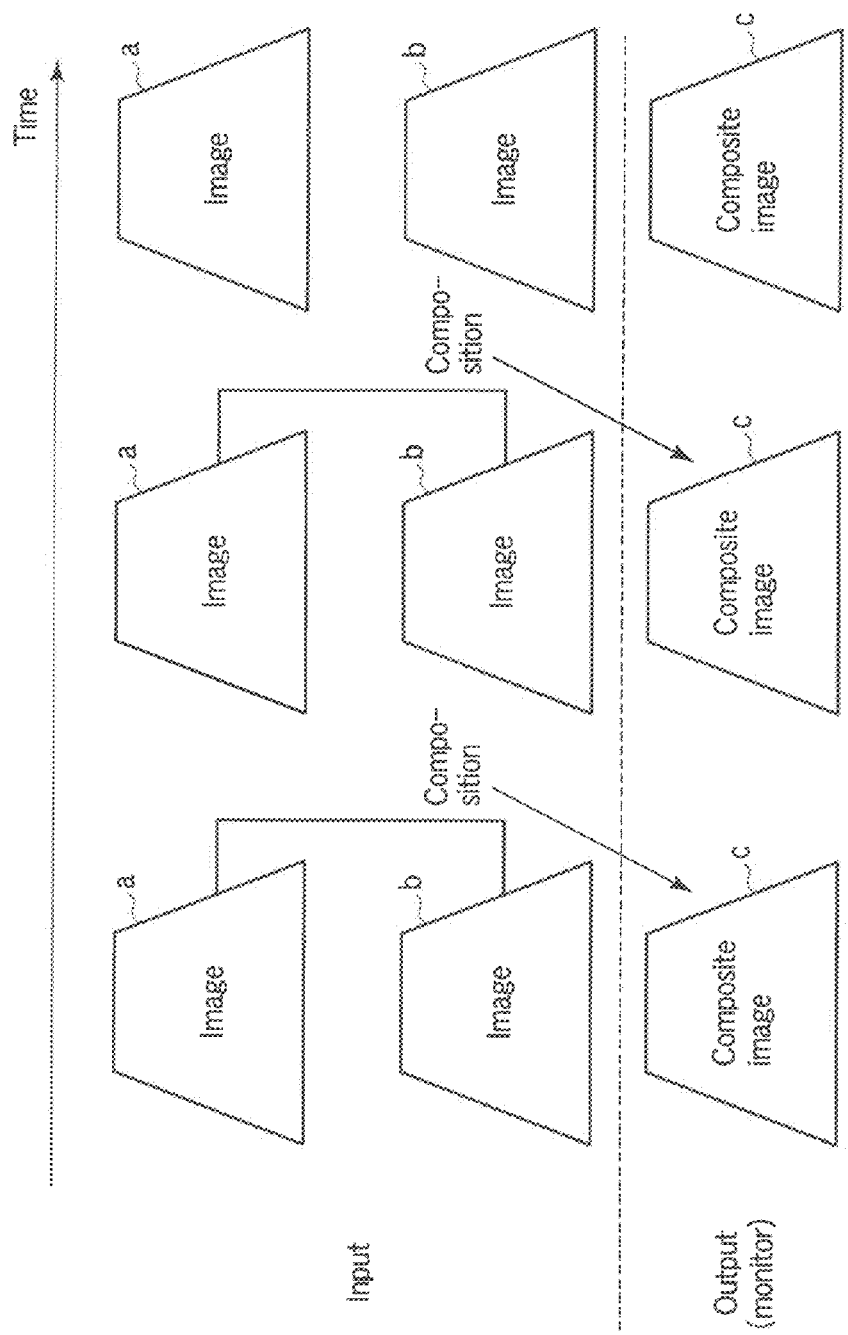
FIG. 4 is a view for explaining the processing of acquiring the images a and b by switching transmission waves for each raster, and generating a composite image c by performing image composition processing for each raster.

In general, according to one embodiment, an ultrasonic diagnosis apparatus which acquires tomographic image data by scanning a predetermined region of an object with an ultrasonic wave has the following arrangement. That is, the ultrasonic diagnosis apparatus includes an ultrasonic probe configured to transmit an ultrasonic wave to the object and receive an echo signal from inside the object, a first transmission wave generating unit configured to generate, as a transmission wave for the scanning, a first transmission wave for acquisition of an image with a higher priority on sensitivity than on resolution, a second transmission wave generating unit configured to generate, as a transmission wave for the scanning, a second transmission wave for acquisition of an image with a higher priority on resolution than on sensitivity, a multiresolution analysis unit configured to perform multiresolution analysis based on predetermined transform processing on the first image acquired by scanning using the first transmission wave and the second image acquired by scanning using the second transmission wave, a filter operation unit configured to perform predetermined filter operation for corresponding coefficients of the first image and the second image for each coefficient of each resolution acquired by the multiresolution analysis unit by the predetermined transform processing, and an inverse transform unit configured to generate a composite image of the first image and the second image by performing inverse transform processing of transform processing by the multiresolution analysis unit for an operation result obtained by the filter operation unit.

FIG. 1 is a block diagram showing the system configuration of an ultrasonic diagnosis apparatus 10 according to this embodiment. As shown in FIG. 1, the ultrasonic diagnosis apparatus 10 includes an ultrasonic probe 12, an input device 13, a monitor 14, a transmission/reception unit 21, a B-mode processing unit 22, a Doppler processing unit 23, an image generating circuit 24, a control processor 25, an internal storage device 26, an interface 29, a storage unit 30, and a position sensor unit 31.

Obviously, the transmission/reception unit 21 and the like may be implemented by hardware such as integrated circuits or may be implemented by software modules as software programs.

The ultrasonic probe 12 is a device (probe) in charge of transmitting and receiving ultrasonic signals applied/reflected to/from an object P based on driving signals from the transmission/reception unit 21, and is formed by a piezoelectric element such as a piezoelectric ceramic element serving as an electromechanical reversible transducer element. The ultrasonic probe 12 is of, for example, a phased array type that has, on its distal end portion, a plurality of piezoelectric elements arranged in an array. With this arrangement, the ultrasonic probe 12 converts an applied pulse driving voltage into an ultrasonic pulse signal, transmits it in a desired direction in a scan area of an object, and converts an ultrasonic signal reflected by the object into an echo signal with a voltage corresponding to the ultrasonic signal.

Assume that the ultrasonic probe 12 is, for example, a two-dimensional array probe (a probe having ultrasonic transducers arranged in a matrix form) capable of three-dimensionally scanning an object. Obviously, however, the ultrasonic probe 12 may be a one-dimensional array probe (a probe having ultrasonic transducers arranged along one direction) configured to perform three-dimensional scanning by a manual, mechanical, or divergent beam system.

The input device 13 is connected to the ultrasonic diagnosis apparatus 10 and includes a trackball 13a and various switches 13b for inputting, to the ultrasonic diagnosis apparatus 10, various instructions from the operator, an instruction to set a region of interest (ROI), and various instructions to set various image quality conditions.

The monitor 14 displays images of morphological information, blood flow information, and the like inside a living body based on video signals generated by the image generating circuit 24.

The transmission/reception unit 21 includes a pulser circuit, delay circuit, trigger generating circuit, amplifier circuit, A/D converter, and adder all of which are not shown. The pulser circuit repetitively generates rate pulses for the formation of transmission ultrasonic waves at a predetermined rate frequency fr Hz (period: 1/fr sec). The delay circuit gives each rate pulse a delay time necessary to focus an ultrasonic wave into a beam and determine transmission directivity for each channel. The trigger generating circuit applies a driving pulse to the ultrasonic probe 12 at the timing based on this rate pulse. The amplifier circuit amplifies an echo signal received through the ultrasonic probe 12 for each channel. The A/D converter gives each amplified echo signal a delay time necessary to determine reception directivity. The adder then performs addition processing to enhance the reflection component of the echo signal from the direction corresponding to the reception directivity, and forms a synthetic beam for ultrasonic transmission/reception in accordance with the reception directivity and transmission directivity.

Note that the transmission/reception unit 21 has a function of instantly changing a transmission frequency, transmission driving voltage, or the like to execute a predetermined scan sequence in accordance with an instruction from the control processor 25.

The B-mode processing unit 22 performs logarithmic amplification and envelope detection processing for the echo signal output from the transmission/reception unit 21 to generate data whose signal intensity is expressed by a luminance level. This data is output to the image generating circuit 24. The monitor 14 then displays the data as a B-mode image representing the intensity of a reflected wave by luminance.

The Doppler processing unit 23 frequency-analyzes velocity information and outputs, to the image generating circuit 24, the analysis result as a signal carrying blood flow or tissue moving velocity information inside the object.

The image generating circuit 24 performs coordinate conversion of output signals from the B-mode processing unit 22 and the Doppler processing unit 23 into display coordinates, and performs various kinds of image processing and composition processing associated with a B-mode image and CFM (Color Flow Mapping) image. The image generating circuit 24 further performs various kinds of quantitative analyses and measurements based on these images, and performs image processing such as adding information indicating the respective results to the images. The image generating circuit 24 then converts the resultant image signals into scan signals for TV and outputs them as video signals to the monitor 14.

Note that when performing multiplane display based on three-dimensional scanning (displaying a plurality of ultrasonic images associated with different slices), the image generating circuit 24 generates image data for sequentially or simultaneously displaying images of a plurality of slices obtained by three-dimensional scanning in a predetermined form.

The control processor 25 is a control unit which has a function as an information processing apparatus (computer) and comprehensively controls the operation of the ultrasonic diagnosis apparatus 10. The control processor 25 reads out control programs for the execution of image generating/display operation from the internal storage device 26 as needed. The control processor 25 expands the control program in a memory area which it has, and executes arithmetic operation/control operation and the like associated with various kinds of processing.

The internal storage device 26 stores control programs for the execution of a predetermined scan sequence, image generation, and display processing, diagnosis information (a patient ID, findings by a doctor, and the like), a diagnosis protocol, transmission/reception conditions, and other data. Note it is possible to transfer data stored in the internal storage device 26 to an external peripheral apparatus via the interface 29.

The interface 29 is an interface for connection to the input device 13, a network, an external storage device (not shown), and the like. Note that the interface 29 can transfer data such as ultrasonic images, analysis results, and the like acquired by the ultrasonic diagnosis apparatus 10 to another apparatus via a network.

The storage unit 30 includes an image memory 30a to store the images acquired by the ultrasonic diagnosis apparatus 10 and various kinds of images acquired via a network and a software storage unit 30b to store software for causing the ultrasonic diagnosis apparatus 10 to function.

The position sensor unit 31 is a sensor unit for detecting the position and direction of the ultrasonic probe 12.

This embodiment is configured to perform composition processing of images acquired by scanning using different kinds of transmission waves. FIG. 2 is a view showing the principle of image composition processing by the image generating circuit 24 in the ultrasonic diagnosis apparatus 10 according to the embodiment. The above image composition processing will be described by taking, as an example, a case in which two images, namely images a and b, are composited.

First of all, the image generating circuit 24 uses an ultrasonic wave having a transmission waveform with a relatively long wave train length as a transmission wave, and extracts only signal components in the second harmonic band from a reception wave through a bandpass filter, thereby acquiring the image a which is a sensitivity-priority image. Note that it is possible to receive second harmonic components with high sensitivity by using a phase modulation technique (called phase inversion, phase modulation, phase subtraction, and the like). The image generating circuit 24 then uses an ultrasonic wave having a transmission waveform with a relatively short wave train length as a transmission wave, and visualizes the second harmonic band like the image a, thereby obtaining the image b which is a resolution-priority image.

The image generating circuit 24 uses a transmission sequence of switching between transmission of a transmission wave for the acquisition of the image a and transmission of a transmission wave for the acquisition of the image b frame by frame. Obviously, it is possible to switch transmission and reception raster by raster.

The image generating circuit 24 performs coordinate conversion of the images acquired by the respective types of scanning and then performs multiresolution analysis of the two consecutive images. In addition, to perform multiresolution analysis, two-dimensional discrete wavelet transform at an L level (for example, about 2 or 3) is performed. This operation will be described in detail below.

The following is a case in which two-dimensional discrete wavelet transform at level 3 is performed to perform multiresolution analysis of the images a and b.

First of all, the image generating circuit 24 performs two-dimensional discrete wavelet transform (dwt) at level 1 to decompose each of the images a and b into wavelet coefficients A1 (Approximation), H1 (Horizontal detail), V1 (Vertical detail), and D1 (Diagonal detail) (the respective wavelet coefficients of the image a will be referred to as A1a, H1a, V1a, and D1a, and the respective wavelet coefficients of the image b will be referred to as A1b, H1b, V1b, and D1b; that is, ○○a and ○○b respectively represent coefficients ○○ of the images a and b).

The image generating circuit 24 then obtains A2, H2, V2, and D2 by further performing two-dimensional discrete wavelet transform of A1. The image generating circuit 24 obtains A3, H3, V3, and D3 by further performing two-dimensional discrete wavelet transform of A2. The above processing is performed for both the images a and b.

In this case, new coefficients are generated by performing predetermined arithmetic operations using the corresponding wavelet coefficients. As the predetermined arithmetic operations, for example, the following arithmetic operations can be presented:

setting A3=A3a, or executing Mean(A3a, A3b), or increasing the ratio of A3a like 0.8*A3a+0.2*A3b, and adding/averaging the corresponding wavelet coefficients;

setting H3=H3b or increasing the ratio of H3b, and adding/averaging the corresponding wavelet coefficients;

setting V3=V3b or increasing the ratio of V3b, and adding/averaging the corresponding wavelet coefficients;

setting D3=D3b or increasing the ratio of D3b, and adding/averaging the corresponding wavelet coefficients;

setting H2=H2b or increasing the ratio of H2b, and adding/averaging the corresponding wavelet coefficients;

setting V2=V2b or increasing the ratio of V2b, and adding/averaging the corresponding wavelet coefficients;

setting D2=D2b or increasing the ratio of D2b, and adding/averaging the corresponding wavelet coefficients;

setting H1=H1b or increasing the ratio of H1b, and adding/averaging the corresponding wavelet coefficients;

setting V1=V1b or increasing the ratio of V1b, and adding/averaging the corresponding wavelet coefficients; and setting D1=D1b or increasing the ratio of D1b, and adding/averaging the corresponding wavelet coefficients.

In this case, Mean(a, b) represents the arithmetic operation of calculating the average value of coefficients ○○ of the images a and b. Note that if b=0, it is possible to output the value of a, whereas if a=0, it is possible to output the value of b.

Upon performing the above arithmetic operations, the image generating circuit 24 calculates the coefficient A2 by performing two-dimensional inverse discrete wavelet transform (idwt) for the coefficients A3, H3, V3, and D3. The image generating circuit 24 further calculates the coefficient A1 by performing two-dimensional inverse discrete wavelet transform for the coefficients A2, H2, V2, and D2. The image generating circuit 24 then obtains a composite image from the coefficients A1, H1, V1, and D1 by performing two-dimensional inverse discrete wavelet transform.

The above image composition processing will be described in detail below. This processing will be described by taking, as an example, a case in which arithmetic operations are performed for two frames for each wavelet coefficient.

First of all, assume that the arithmetic function to be used is func(a1, a2, ..., aN, M, Level), where a1, a2, ..., aN represent input data, M=0 represents Approximation, M=1 represents Horizontal detail, M=2 represents Vertical detail, M=3 represents Diagonal detail, and Level represents a wavelet expansion count. In addition idwt2 represents two-dimensional inverse discrete wavelet transform.

The above arithmetic operations are represented by

A(L)=func(A(L,n),A(L,n−1), . . . ,A(L,n−k),0,L)
H(L)=func(H(L,n),H(L,n−1), . . . ,H(L,n−k),1,L)
V(L)=func(V(L,n),V(L,n−1), . . . ,V(L,n−k),2,L)
D(L)=func(D(L,n),D(L,n−1), . . . ,D(L,n−k),3,L)
H(L−1)=func(H(L−1,n),H(L−1,n−1), . . . ,H(L−1,n−k),1,L−1)
V(L−1)=func(V(L−1,n),V(L−1,n−1), . . . ,V(L−1,n−k),2,L−1)
D(L−1)=func(D(L−1,n),D(L−1,n−1), . . . ,D(L−1,n−k),3,L−1)
. . .
H(1)=func(H(L,n),H(L,n−1), . . . ,H(L,n−k),1,1)
V(1)=func(V(L,n),V(L,n−1), . . . ,V(L,n−k),2,1)
D(1)=func(D(L,n),D(L,n−1), . . . ,D(L,n−k),3,1)
A(L−1)=idwt2(A(L),H(L),V(L),D(L))
A(L−2)=idwt2(A(L−1),H(L−1),V(L−1),D(L−1))
. . .
A(0)=idwt2(A(1),H(1),V(1),D(1))

In this case, A(0) represents an image after composition processing.

The following is an example of the arithmetic functions. That is, at all Levels, func(a1, a2, . . . , aN, M, Level)=a M=0
func(a1, a2, . . . , aN, M, Level)=a2 M=1, 2, 3

That is, with regard to Approximation, arithmetic operations are performed by using the coefficients of the image a. With regard to other coefficients, arithmetic operations are performed by using the coefficients of the image b. Obviously, it is possible to execute adding/averaging processing with predetermined allocation ratios instead of using one of the sets of the coefficients of the images a and b. It is also possible to set allocation ratios in such adding/averaging processing to the values desired by the user. It is obviously possible to provide an operation unit or the like to allow the user to perform such setting.

As described above, using the coefficients of the image a with regard to "Approximation" coefficient can obtain a rough luminance distribution and structure of an image from the image a. On the other hand, since the information of the image b is reflected in "detail" coefficients of H, V, D, the resultant image will inherit the apparent granularity and the like of the image b.

In this case, the following merit is obtained when acquiring the images a and b by switching the above transmission waves frame by frame and generating a composite image c by performing the above image composition processing between two consecutive frames, as shown in, for example, FIG. 3. When the monitor 14 displays the composite image generated by the above processing, the apparent frame rate does not change.

On the other hand, assume that the images a and b are acquired by switching transmission waves alternately for each raster, and the composite image c is generated by performing the above composition processing for each raster, as shown in, for example, FIG. 4. A merit of this processing is that when the monitor 14 displays the generated composite image, the time phase shift in a frame is small. In this case, however, the frame rate decreases.

To overcome this problem, it is possible to suppress a decrease in frame rate by changing the number of rasters for the images a and b (reducing the number of transmission wave rasters of the image a to almost half). Since high resolution is not required for the image a, reducing the number of transmission wave raters to about half will pose no problem.

In the above case, although arithmetic operations are performed by using only the coefficient of each pixel, it is obviously possible to perform arithmetic operations by using the coefficients of neighboring pixels. For example, as a method of calculating the "AbsMax" of two images at position (x, y), it is possible to use a method of calculating an average value a1 of neighboring 5×5 points including (x, y) of the first image, calculating an average value a2 of neighboring 5×5 points including (x, y) of the second image, and using a larger one of the absolute values of a1 and a2 as an output value at (x, y).

The above sequence of image composition processing performed by the ultrasonic diagnosis apparatus according to this embodiment can be easily on sale and distributed as a single software product independent of the ultrasonic diagnosis apparatus by programming the sequence or storing the resultant program in a storage medium. In addition, the technique according to the embodiment can be used on other hardware.

As described above, this embodiment can provide an ultrasonic diagnosis apparatus and program which can acquire a video satisfying both the requirements for sensitivity (luminance) and resolution (visibility).

More specifically, it is possible to generate an image inheriting both the merits of the images a and b by performing arithmetic operations of mainly outputting the coefficients of the image a with high sensitivity (high luminance) with regard to low-frequency components acquired by wavelet transform and mainly outputting the coefficients of the image b with high resolution (high visibility) with regard to high-frequency components. Therefore, the merits of two images having different advantages can be expressed on one image. This contributes to an improvement in examination efficiency and diagnosis efficiency.

Obviously, it is also possible to perform filter processing for edge enhancement and speckle reduction in combination with the above image composition processing by the ultrasonic diagnosis apparatus according to the above embodiment. This processing will be described in detail below.

[First Modification]

This apparatus may perform processing as a combination of multiresolution analysis like that disclosed in, for example, Jpn. Pat. Appln. KOKAI Publication No. 2006-116307 and a nonlinear diffusion filter like that described below before the above image composition processing. Performing such processing can generate a more viewable image with less speckle and enhanced edges.

A speckle removal function using a nonlinear diffusion filter will be described in detail below. This speckle removal function acquires low-frequency decomposed image data at the first to nth levels (where n is a natural number equal to or more than two) and high-frequency decomposed image data at the first to nth levels by hierarchically performing multi-resolution decomposition of image data (raw data) before so-called scan conversion processing by the image generating circuit 24. The function then performs nonlinear anisotropic diffusion filtering for output data from the next lower layer or the low-frequency decomposed image data on the lowest layer, and filtering for generating edge information of a signal for each layer from the output data from the next lower layer or the low-frequency decomposed image data on the lowest layer.

This function also controls the signal level of the high-frequency decomposed image data for each layer based on the edge information on each layer and hierarchically performs multiresolution composition of the output data from the nonlinear anisotropic diffusion filter and the output data of the high-frequency level control, which are obtained on each layer. Performing such processing will remove speckle by the synergetic effect of the multiresolution decomposition and the nonlinear anisotropic diffusion filter processing. For the sake of a concrete description, this embodiment will exemplify a case in which the number n of levels of multiresolution decomposition is 3. However, this case is merely an example, and the number n may be any value as long as it is a natural number equal to or more than two, for example.

FIG. 5 is a block diagram showing an example of the system configuration of an ultrasonic diagnosis apparatus according to this modification. The main difference between the ultrasonic diagnosis apparatus according to this modification and the ultrasonic diagnosis apparatus according to the above embodiment is whether they include a speckle removal processing unit 46.

Figure 6:
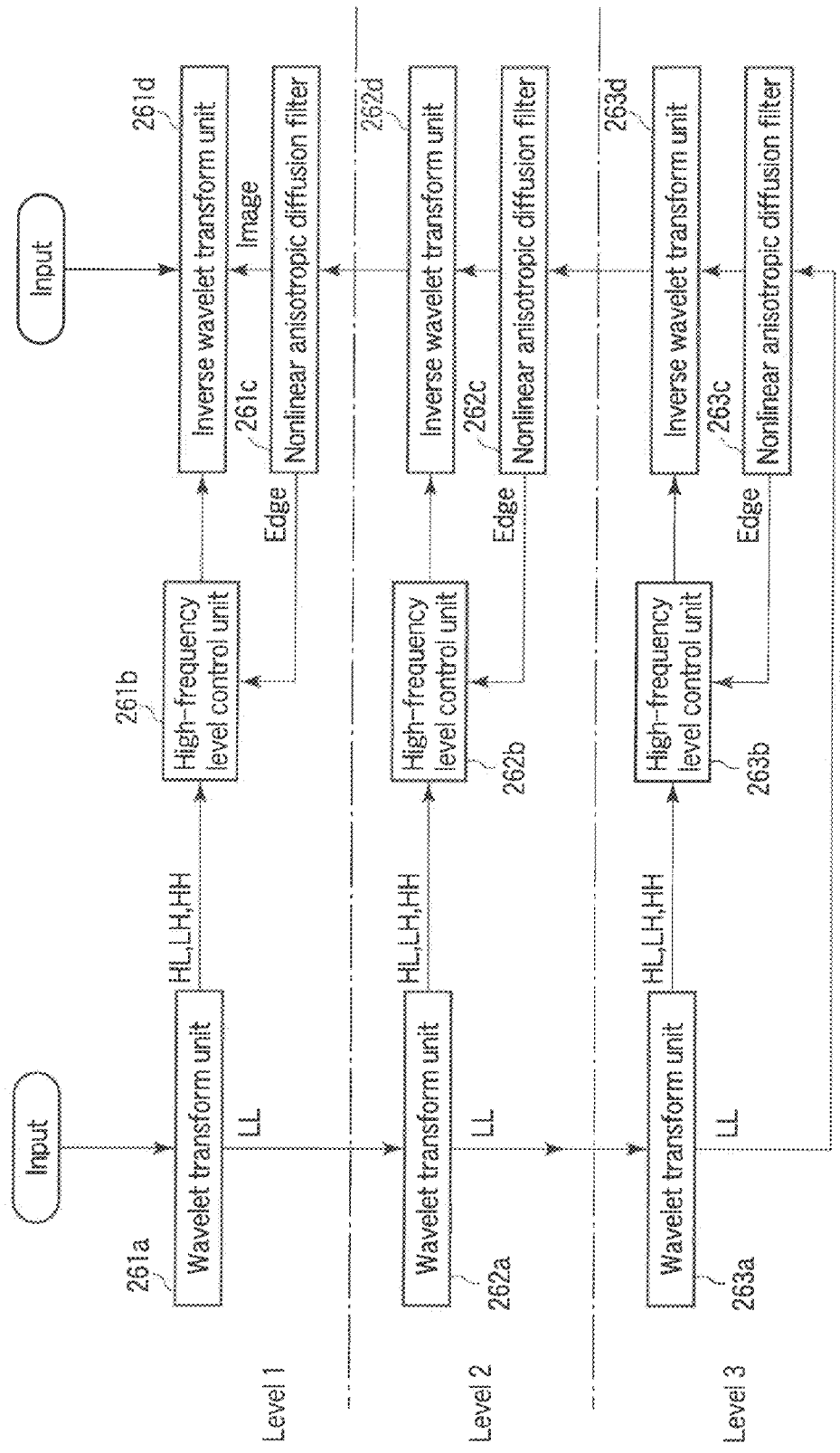
FIG. 6 is a view showing a processing (speckle removal processing) procedure based on a speckle removal function executed by a speckle removal processing unit.

FIG. 6 is a view showing processing (speckle removal processing) procedure executed by the speckle removal processing unit 46.

As shown in FIG. 6, first of all, a wavelet transform unit 261a of level 1 performs multiresolution decomposition of image data (raw data) input from the B-mode processing unit 22. In this case, "wavelet transform" means discrete wavelet transform. In addition, wavelet transform is an example of multiresolution decomposition, and the technical idea of the present invention is not limited to this technique. For example, multiresolution decomposition may be implemented by other techniques such as the Laplacian pyramid method.

As a result of the multiresolution decomposition, image data after decomposition is decomposed into a low-frequency image LL, a horizontal high-frequency image LH, a vertical high-frequency image HL, and a diagonal high-frequency image HH, of which horizontal and vertical lengths are half of those before the decomposition. Among the image data acquired by the decomposition, the wavelet transform unit 261a outputs the low-frequency image LL to a wavelet transform unit 262a of level 2 and outputs the horizontal high-frequency image LH, the vertical high-frequency image HL, and the diagonal high-frequency image HH to a high-frequency level control unit 261b.

The wavelet transform unit 262a of level 2 acquires the low-frequency image LL, the horizontal high-frequency image LH, the vertical high-frequency image HL, and the diagonal high-frequency image HH by performing multiresolution decomposition of the low-frequency image LL output from the wavelet transform unit 261a of level 1. The wavelet transform unit 262a outputs the low-frequency image LL to a wavelet transform unit 263a of level 2 and outputs the horizontal high-frequency image LH, the vertical high-frequency image HL, and the diagonal high-frequency image HH to a high-frequency level control unit 262b.

The wavelet transform unit 263a of level 2 acquires the low-frequency image LL, the horizontal high-frequency image LH, the vertical high-frequency image HL, and the diagonal high-frequency image HH by performing multiresolution decomposition of the low-frequency image LL output from the wavelet transform unit 262a of level 2. The wavelet transform unit 263a outputs the low-frequency image LL to a nonlinear anisotropic diffusion filter 263c of level 3, and outputs the horizontal high-frequency image LH, the vertical high-frequency image HL, and the diagonal high-frequency image HH to a high-frequency level control unit 263b.

The nonlinear anisotropic diffusion filter 263c of level 3 then performs filtering of the low-frequency image LL and outputs the low-frequency image LL after the filtering to an inverse wavelet transform unit 263d. In addition, the nonlinear anisotropic diffusion filter 263c of level 3 generates edge information based on the low-frequency image LL and outputs the information to the inverse wavelet transform unit 263d.

A nonlinear anisotropic diffusion filter will be described below. The nonlinear anisotropic diffusion filter is expressed by the following partial differential equation (1).

$$\frac{\partial I}{\partial t} = div[D\nabla I] \tag{1}$$

where I is the pixel level of an image to be processed, $\nabla I$ is the gradient vector of the image, t is the time for the processing, and D is diffusion tensor, which can be expressed by the following expression (2).

$$D = \begin{pmatrix} d_{11} & d_{12} \\ d_{12} & d_{22} \end{pmatrix} = R \begin{pmatrix} \lambda_1 & 0 \\ 0 & \lambda_2 \end{pmatrix} R^T \tag{2}$$

where R is a rotation matrix. The diffusion tensor D indicates an arithmetic operation of applying coefficients $\lambda 1$ and $\lambda 2$ to the gradient vector of each pixel in a specific direction and a direction perpendicular to the specific direction. The direction is the direction of the edge of a detected image, and the coefficient depends on the size of the edge.

In order to detect the size and direction of the edge, it is general to acquire the structure tensor of the image and calculate its eigenvalue and eigenvector. The eigenvalue is associated with the size of the edge, and the eigenvector indicates the direction of the edge. The structure tensor is defined by equation (3) given below.

$$S = G_\rho * \begin{pmatrix} I_x^2 & I_x I_y \\ I_x I_y & I_y^2 \end{pmatrix} = \begin{pmatrix} G_\rho * I_x^2 & G_\rho * (I_x I_y) \\ G_\rho * (I_x I_y) & G_\rho * I_y^2 \end{pmatrix} = \begin{pmatrix} s_{11} & s_{12} \\ s_{12} & s_{22} \end{pmatrix} \tag{3}$$

where Ix and Iy represent spatial differentiation of the image I to be processed in the x (horizontal) and y (vertical) directions, Gp represents a two-dimensional Gaussian function, and an operator "*" represents convolution. The calculation of the size and direction of an edge need not strictly follow the above method. Instead of calculating Ix and Iy as the first step in processing, a sobel filter or a high-frequency component of multiresolution decomposition may be applied.

Although the method of calculating the coefficients $\lambda 1$ and $\lambda 2$ differs depending on the characteristics of an ultrasonic image in each diagnostic field, it is useful to prepare a general expression so that the coefficients can be adjusted by some parameters.

In addition, the calculation of the filter itself is performed by a numerical analysis method using a partial differential equation. That is, from the pixel level of a pixel at a given point and pixel levels of, for example, pixels at nine points around the pixel and each element value of diffusion tensor at time t, a new pixel level at the point at time t+Δt is calculated. The same calculation is then repeated once to several times with t+Δt as new t.

Figure 7:
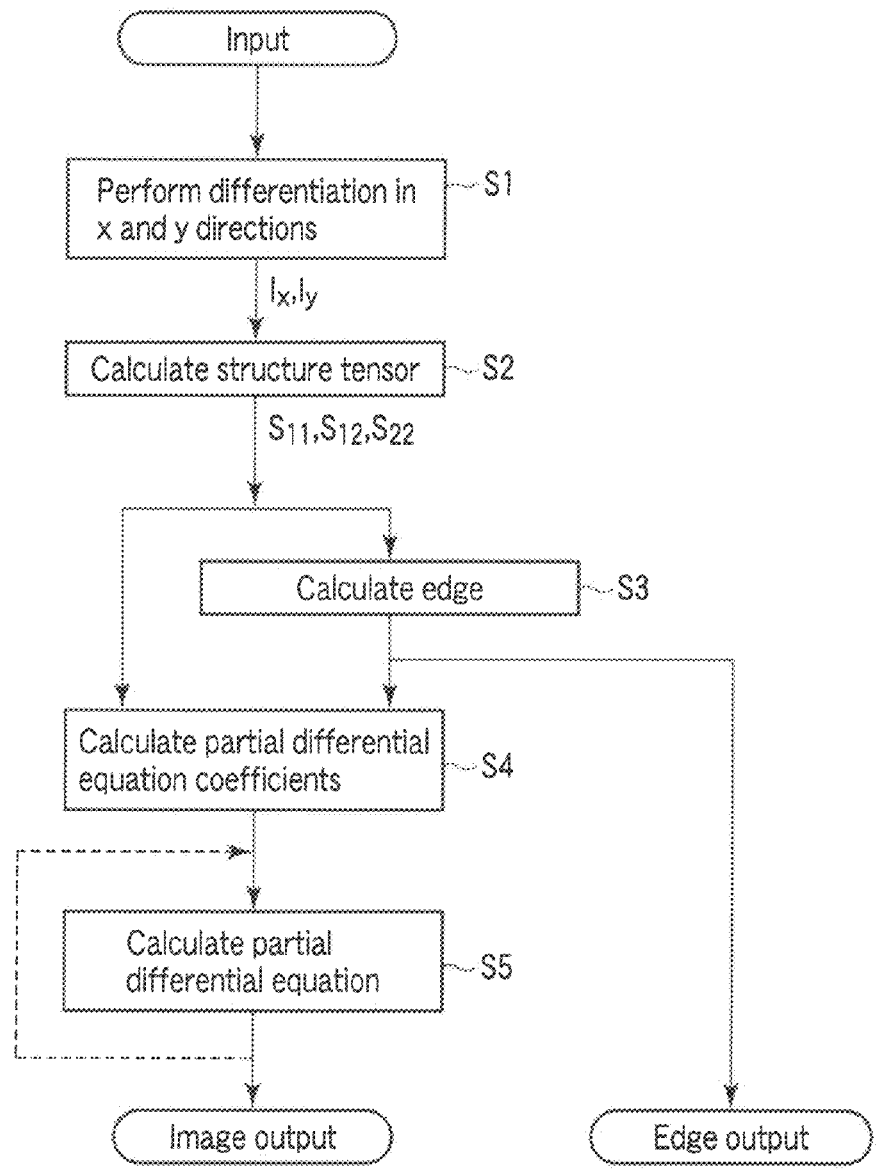
FIG. 7 is a flowchart showing a filter processing procedure executed by a nonlinear anisotropic diffusion filter.

FIG. 7 is a flowchart showing a filter processing procedure executed by the nonlinear anisotropic diffusion filter 263c (or 261c or 262c). As shown in FIG. 7, the nonlinear anisotropic diffusion filter 263c differentiates the input low-frequency image LL in the x and y directions (step S1) and calculates structure tensors s11, s12, and s22 (step S2). Note that the calculation in step S2 also includes calculation using a Gaussian filter.

The nonlinear anisotropic diffusion filter 263c calculates the size of the edge from each element of the structure tensor (step S3). This calculation result is used for partial differential equation calculation in a subsequent stage and processing in the high-frequency level control unit 263b (or 262b or 261b).

The nonlinear anisotropic diffusion filter 263c then calculates each coefficient used in the numerical analysis of the partial differential equation of the nonlinear anisotropic diffusion filter based on each element of the structure tensor (step S4). In addition, the processing in this step also includes the calculation of the structure tensor, and also uses the size of the edge in the calculation for efficient processing.

The nonlinear anisotropic diffusion filter 263c repeatedly executes numerical-analytical calculation of the partial differential equation once or several times (step S5). The result obtained by the calculation is output to the inverse wavelet transform unit 263d (or 261d or 262d).

As shown in FIG. 6, the high-frequency level control unit 263b of level 3 receives the horizontal high-frequency image LH, the vertical high-frequency image HL, the diagonal high-frequency image HH, and edge information associated with these three components and controls a high-frequency level according to the images and the edge information. In this embodiment, the edge information is the size of an edge normalized based on the eigenvalue of the structure tensor, a product of the size and each high-frequency image is calculated for each pixel, and a control coefficient of each high-frequency image is applied to the result.

As another example, there is a method of setting a threshold for the size of an edge, determining that a given portion is an edge when its size is equal to or more than the threshold, and applying a control coefficient of each high-frequency image to a region other than the edge. Three high-frequency images processed in this manner are input to the inverse wavelet transform unit 263d.

The inverse wavelet transform unit 263d forms one composite image from the low-frequency image LL output from the nonlinear anisotropic diffusion filter 263c and the horizontal high-frequency image LH, the vertical high-frequency image HL, and the diagonal high-frequency image HH output from the high-frequency level control unit 263b. The horizontal and vertical lengths of the composite image are twice those of an input image.

The composite image output from the inverse wavelet transform unit 263d of level 3 is input to the nonlinear anisotropic diffusion filter 262c of level 2, is subjected to the same filtering processing as that at level 3, and is then transmitted to the low-frequency image input of the inverse wavelet transform unit 262d.

On the other hand, the high-frequency level control unit 262b performs the same high-frequency control as that at level 3 for the horizontal high-frequency image LH, the vertical high-frequency image HL, and the diagonal high-frequency image HH output from the wavelet transform unit 262a. The high-frequency level control unit 262b then transmits the resultant images to the high-frequency image input of the inverse wavelet transform unit 262d. The inverse wavelet transform unit 262d forms one composite image data from one low-frequency image and three high-frequency images in the same manner as level 3.

In addition, the composite image output from the inverse wavelet transform unit 262d of level 2 is input to the nonlinear anisotropic diffusion filter 261 of level 1, is subjected to the same filtering processing as that at levels 2 and 3, and is then transmitted to the low-frequency image input of the inverse wavelet transform unit 261d.

On the other hand, the high-frequency level control unit 261b performs the same high-frequency control as that at levels 2 and 3 for the horizontal high-frequency image LH, the vertical high-frequency image HL, and the diagonal high-frequency image HH output from the wavelet transform unit 261a. The high-frequency level control unit 261b then transmits the resultant images to the high-frequency image input of the inverse wavelet transform unit 261d. The inverse wavelet transform unit 261d forms one composite image data from one low-frequency image and three high-frequency images in the same manner as levels 2 and 3.

The composite image data formed by the above processing is transmitted from the speckle removal processing unit 46 to the image generating circuit 24. The image generating circuit 24 composites the composite image data with character information, scale, and the like of various parameters, converts the result into a scanning line signal string in a general video format typified by a TV format, and generates an ultrasonic diagnostic image as a display image. The monitor 14 displays the generated ultrasonic image in a predetermined form.

As described above, this modification can provide an ultrasonic diagnosis apparatus and program which have the following effects in addition to effects similar to those of the above embodiment.

This ultrasonic diagnosis apparatus hierarchically performs multiresolution decomposition of image data (raw data) before scan conversion processing to acquire low-frequency decomposed image data at the first to nth levels (where n is a natural number equal to or more than two) and high-frequency decomposed image data at the first to nth levels, performs nonlinear anisotropic diffusion filtering for output data from the next lower layer or the low-frequency decomposed image data on the lowest layer, and performs filtering for generating edge information of a signal for each layer from the output data from the next lower layer or the low-frequency decomposed image data on the lowest layer.

In addition, this apparatus controls the signal level of the high-frequency decomposed image data for each layer based on the edge information on each layer and hierarchically performs multiresolution composition of the output data from the nonlinear anisotropic diffusion filter and the output data of the high-frequency level control, which are obtained on each layer. With this processing, the apparatus removes speckle by the synergetic effect of the multiresolution decomposition and the nonlinear anisotropic diffusion filter processing. Therefore, compared with a case in which only a filter is applied, speckle removal processing in which the speckle is fine and an interface of tissues is clearer can be implemented. As a result, a high-quality diagnostic image can be provided, which can contribute to an improvement in the quality of image diagnosis.

In addition, this ultrasonic diagnosis apparatus applies the nonlinear anisotropic diffusion filter after reducing an image by multiresolution decomposition. Accordingly, compared with a case in which a nonlinear anisotropic diffusion filter is applied directly to an original image, the processing area (the amount of data to be processed) can be reduced. As a result, high-speed processing can be implemented compared with a nonlinear anisotropic diffusion filter which requires much time for calculation.

Furthermore, according to the ultrasonic diagnosis apparatus, since only a B-mode image is processed in speckle removal processing, the processing does not influence a color Doppler image even if the color Doppler image is superimposed on the B-mode image. As a result, it is possible to implement high-quality speckle removal without restricting the degree of freedom in image processing or image display and without influencing the processing speed even if the resolution of a display system increases.

Note that the image a with poor resolution has a problem associated with false recognition of an edge, and hence the above filter processing cannot be sometimes be applied strongly. Therefore, when edge information is to be extracted, the information may be calculated from the image b before arithmetic operation between the images, and a smoothing filter may be applied to the image after the arithmetic operation by using the calculation result. This can suppress false recognition of an edge and the like.

The above embodiment and modification use discrete wavelet transform as multiresolution analysis. In general discrete wavelet transform, an LPF (Low Pass Filter) and HPF (High Pass Filter) are applied to information, and the respective outputs are downsampled to half. For this reason, the amount of information does not change before and after the wavelet transform. When inverse wavelet transform is performed after operation of coefficients in wavelet shrinkage, block-like artifact may appear on an image.

In consideration of such a situation, it is conceivable to use stationary wavelet transform as multiresolution analysis instead of discrete wavelet transform.

Stationary wavelet transform is configured not to perform downsampling. For this reason, when, for example, stationary wavelet transform of a two-dimensional image is performed once, the amount of information increases four times. However, even when inverse transform of the image is performed after wavelet shrinkage, any block-like artifact like that described above does not appear.

It is also possible to use one of various types of pyramid transforms such as Laplacian pyramid transform, RoL (Ratio of low pass) pyramid transform, and gradient pyramid transform as multiresolution analysis instead of wavelet transform.

The main difference between wavelet transform and pyramid transform is that wavelet transform is orthogonal transform, but pyramid transform is not necessarily orthogonal transform. However, like wavelet transform, pyramid transform allows multiresolution analysis.

Note that it is possible to apply the above embodiment and modification to image composition processing based on the above frequency compound. When, for example, an amplitude modulation method is to be used, since only bubbles are visualized, only the fundamental wave band can be used. In this case, however, the frequency band is narrow, and hence the obtained image has poor resolution. For this reason, this image is set as the image a, and an image containing up to the second harmonic is set as the image b. The above composition processing is performed for the images a and b to obtain an image with high sensitivity and good resolution. This method need not switch transmission waves, and hence is free from a reduction in frame rate.

The above embodiment includes inventions of various stages, and various inventions can be extracted by proper combinations of a plurality of disclosed constituent elements. Even if, for example, several constituent elements are omitted from all the constituent elements in the embodiment, the problem described in "Description of the Related Art" can be solved. If the effects described above can be obtained, the arrangement from which these constituent elements are omitted can be extracted as an invention.

[Second Modification]

Contrast-enhanced ultrasonography requires good spatial resolution and high contrast-enhanced bubble detection sensitivity, and also requires high separation between contrast-enhanced bubbles and the tissue. The second modification has been made in consideration of this situation.

To avoid a redundant description, the differences between the above embodiment and the first modification will be described below. The ultrasonic diagnosis apparatus and program according to the second modification acquire the images a and b described above by the following processing.

The image a is acquired by a technique known by those skilled in the art as an AM (Amplitude Modulation) method. In the AM method, when repetitively generating rate pulses, the pulser circuit repetitively generates the rate pulses while amplitude-modulating them at a predetermined (e.g., 5-kHz) rate frequency fr Hz (period: 1/fr sec).

The AM method provides superior separation between contrast-enhanced bubbles and the tissue, and exhibits high depth sensitivity.

The image b is acquired by a technique known by those skilled in the art as a PM (Phase Modulation) method. In the PM method, when repetitively generating rate pulses, the pulser circuit repetitively generates the rate pulses while phase-modulating them at a predetermined (e.g., 5-kHz) rate frequency fr Hz (period: 1/fr sec).

The PM method provides superior spatial resolution. However, the PM method is regarded as a method which does not provide superior separation between contrast-enhanced bubbles and the tissue.

Like the above embodiment and the first modification, the second modification switches between transmission of a transmission wave for the acquisition of the image a and transmission of a transmission wave for the acquisition of the image b alternately for each frame or raster. This modification performs multiresolution analysis of the image a obtained by the AM method and the image b obtained by the PM method, and further performs composition processing.

As described above, the second modification can obtain effects similar to those of the ultrasonic diagnosis apparatus and program according to the above embodiment and provide an ultrasonic diagnosis apparatus and program which have the following effects.

The second modification can provide an ultrasonic diagnosis apparatus and program which satisfy both the requirements for sensitivity (luminance) and resolution (visibility) and provide good separation between contrast-enhanced bubbles and the tissue.

In order to reduce the time difference between acquired images, scanning for the acquisition of the image a may be performed with a smaller number of rasters than that of scanning for the acquisition of the image b. In addition, it is possible to provide a UI for changing the composition ratio between the images a and b.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnosis apparatus which acquires tomographic image data by scanning a predetermined region of an object with an ultrasonic wave, the apparatus comprising:
   an ultrasonic probe configured to transmit first transmission waves having different amplitudes and second transmission waves having different phases for each of scanning lines, and to receive first echoes caused by the first transmission waves and second echoes caused by the second transmission waves;
   an image generation unit configured to generate, without use of a Doppler method, a first image based on the first echoes and a second image based on the second echoes, wherein a spatial resolution of the first image is higher than a spatial resolution of the second image and a sensitivity of the second image is higher than a sensitivity of the first image;
   a multiresolution analysis unit configured to perform multiresolution analysis based on predetermined transform processing on the first image and the second image;
   a filter operation unit configured to perform a predetermined filter operation for corresponding coefficients of the first image and the second image for each coefficient of each spatial resolution acquired by the multiresolution analysis unit by the predetermined transform processing; and
   an inverse transform unit configured to generate a composite image of the first image and the second image by performing inverse transform processing of the transform processing by the multiresolution analysis unit for an operation result obtained by the filter operation unit.

2. The apparatus according to claim 1, wherein the multiresolution analysis unit performs, as the predetermined transform processing, any one of wavelet transform, stationary wavelet transform, and pyramid transform.

3. The apparatus according to claim 1, wherein the predetermined filter operation performed by the filter operation unit comprises one of adding or averaging processing of corresponding coefficients of the first image and the second image for each spatial resolution and adding or averaging processing of coefficients with resolutions lower than a predetermined spatial resolution upon increasing a ratio of the first image and adding or averaging processing of coefficients with resolutions higher than a predetermined spatial resolution upon increasing a ratio of the second image.

4. The apparatus according to claim 3, wherein the predetermined filter operation performed by the filter operation unit comprises a filter operation using coefficients of the first image as the coefficients of spatial resolutions lower than the predetermined resolution and using coefficients of the second image as the coefficients with spatial resolutions higher than the predetermined spatial resolution.

5. The apparatus according to claim 1, wherein the first image and the second image comprise images obtained by scanning while switching the first transmission wave and the second transmission wave frame by frame.

6. The apparatus according to claim 1, wherein the first image and the second image comprise images obtained by scanning while switching the first transmission wave and the second transmission wave raster by raster.

7. The apparatus according to claim 1, further comprising an edge processing unit configured to extract edge position information from the second image after processing by the multiresolution analysis unit and before processing by the filter operation unit and perform edge enhancement processing or edge preserving smoothing filter processing for each coefficient of the first image based on the extracted edge information.

8. The apparatus according to claim 1, wherein a wave train length of the first transmission wave is longer than a wave train length of the second transmission wave.

9. The apparatus according to claim 1, wherein the sensitivity indicates a detectability of injected contrast medium bubbles.

10. The apparatus according to claim 1, wherein the number of the first transmission waves transmitted by the ultrasonic probe is ½ the number of the second transmission waves generated transmitted by the ultrasonic probe.

11. An ultrasonic diagnosis apparatus which acquires tomographic image data by scanning a predetermined region of an object, in which region a contrast medium has been injected, with an ultrasonic wave, the apparatus comprising:
   an ultrasonic probe configured to transmit first transmission waves having different amplitudes and second transmission waves having different phases for each of scanning lines, and to receive first echoes caused by the first transmission waves and second echoes caused by the second transmission waves;
   an image generation unit configured to generate, without use of a Doppler method, a first image based on the first echoes and a second image based on the second echoes, wherein a spatial resolution of the first image is higher than a spatial resolution of the second image and a sensitivity of the second image is higher than a sensitivity of the first image;
   a multiresolution analysis unit configured to perform multiresolution analysis based on predetermined transform processing on a first image and a second image;
   a filter operation unit configured to perform predetermined filter operation for corresponding coefficients of the first image and the second image for each coefficient of each spatial resolution acquired by the multiresolution analysis unit by the predetermined transform processing; and
   an inverse transform unit configured to generate a composite image of the first image and the second image by performing inverse transform processing of transform processing by the multiresolution analysis unit for an operation result obtained by the filter operation unit.

12. A non-transitory computer readable medium including computer executable instructions which cause a computer to function as an ultrasonic diagnosis apparatus which acquires tomographic image data by scanning a predetermined region of an object with an ultrasonic wave, the program causing the computer to implement:
   a function of transmitting first transmission waves having different amplitudes and second transmission waves having different phases for each of scanning lines, and receiving first echoes caused by the first transmission waves and second echoes caused by the second transmission waves,
   an image generation function to generate, without use of a Doppler method, a first image based on the first echoes and a second image based on the second echoes, wherein a spatial resolution of the first image is higher than a spatial resolution of the second image and a sensitivity of the second image is higher than a sensitivity of the first image;
   a multiresolution analysis function of performing multiresolution analysis based on predetermined transform processing on the first image and the second image, a filter operation function of performing predetermined filter operation for corresponding coefficients of the first image and the second image for each coefficient of each spatial resolution acquired by the multiresolution analysis function by the predetermined transform processing, and an inverse transform function of generating a composite image of the first image and the second image by performing inverse transform processing of transform processing by the multiresolution analysis function for an operation result obtained by the filter operation function.

13. A non-transitory computer readable medium including computer executable instructions which cause a computer to function as an ultrasonic diagnosis apparatus which acquires tomographic image data by scanning a predetermined region of an object, in which a contrast medium has been injected, with an ultrasonic wave, the program causing the computer to implement:

a function of transmitting first transmission waves having different amplitudes and second transmission waves having different phases for each of scanning lines, and receiving first echoes caused by the first transmission waves and second echoes caused by the second transmission waves, an image generation function to generate, without use of a Doppler method, a first image based on the first echoes and a second image based on the second echoes, wherein a spatial resolution of the first image is higher than a spatial resolution of the second image and a sensitivity of the second image is higher than a sensitivity of the first image, a multiresolution analysis function of performing multiresolution analysis based on predetermined transform processing on a first image and a second image, a filter operation function of performing predetermined filter operation for corresponding coefficients of the first image and the second image for each coefficient of each spatial resolution acquired by the multiresolution analysis function by the predetermined transform processing, and an inverse transform function of generating a composite image of the first image and the second image by performing inverse transform processing of transform processing by the multiresolution analysis function for an operation result obtained by the filter operation function.

14. The apparatus according to claim 1, wherein the first transmission wave is generated by an amplitude modulation and the second transmission wave is generated by a phase modulation.

* * * * *